(12) United States Patent  (10) Patent No.: US 8,394,091 B2
Rioux et al.                  (45) Date of Patent:     Mar. 12, 2013

(54) MAGNETICALLY STEERABLE CATHETER ASSEMBLY

(75) Inventors: Robert Rioux, Ashland, MA (US); Thomas V. Casey, Grafton, MA (US)

(73) Assignee: Boston Scientific Scimed, Inc., Maple Grove, MA (US)

( * ) Notice: Subject to any disclaimer, the term of this patent is extended or adjusted under 35 U.S.C. 154(b) by 1004 days.

(21) Appl. No.: 12/196,607

(22) Filed: Aug. 22, 2008

(65) Prior Publication Data

US 2009/0062789 A1   Mar. 5, 2009

Related U.S. Application Data

(60) Provisional application No. 60/957,999, filed on Aug. 24, 2007.

(51) Int. Cl.
A61B 18/14 (2006.01)
(52) U.S. Cl. ............................... 606/41; 604/95.01
(58) Field of Classification Search .................. 606/32, 606/41; 600/12, 146, 434; 607/99
See application file for complete search history.

(56) References Cited

U.S. PATENT DOCUMENTS

| | | | |
|---|---|---|---|
| 5,383,874 A | 1/1995 | Jackson et al. | |
| 5,456,682 A | 10/1995 | Edwards et al. | |
| 5,582,609 A | 12/1996 | Swanson et al. | |
| 5,755,715 A | 5/1998 | Stern et al. | |
| 5,991,650 A | 11/1999 | Swanson et al. | |
| 6,961,620 B2 | 11/2005 | Rioux et al. | |
| 7,172,622 B2 * | 2/2007 | Weber et al. | 623/1.12 |
| 2002/0019644 A1 * | 2/2002 | Hastings et al. | 606/159 |
| 2004/0158142 A1 * | 8/2004 | Hall et al. | 600/374 |
| 2005/0004585 A1 | 1/2005 | Hall et al. | |
| 2005/0021063 A1 | 1/2005 | Hall et al. | |
| 2007/0093808 A1 * | 4/2007 | Mulier et al. | 606/41 |
| 2007/0106143 A1 * | 5/2007 | Flaherty | 600/373 |
| 2007/0123964 A1 * | 5/2007 | Davies et al. | 607/116 |

FOREIGN PATENT DOCUMENTS

| | | |
|---|---|---|
| WO | WO 01/03589 A1 | 1/2001 |
| WO | WO 01/24685 A2 | 4/2001 |
| WO | WO 2006/116735 A1 | 11/2006 |
| WO | WO 2007/025046 A1 | 3/2007 |

OTHER PUBLICATIONS

PCT International Search Report for PCT/US2008/074023, Applicant: Boston Scientific Scimed, Inc., Form PCT/ISA/210 and 220, dated Oct. 15, 2008 (8 pages).
PCT Written Opinion of the International Search Authority for PCT/US2008/074023, Applicant: Boston Scientific Scimed, Inc., Form PCT/ISA/237, dated Oct. 15, 2008 (5 pages).
PCT International Preliminary Report on Patentability (Chapter I of the Patent Cooperation Treaty) for PCT/US2008/074023, Applicant: Boston Scientific Scimed, Inc., Form PCT/IB/326 and 373, dated Feb. 24, 2010 (8 pages).

* cited by examiner

*Primary Examiner* — Michael Peffley
*Assistant Examiner* — Thomas Giuliani
(74) *Attorney, Agent, or Firm* — Vista IP Lawgroup LLP

(57) ABSTRACT

A magnetically steerable catheter system and method of using the system is provided. The system comprises an outer elongated, flexible member having a proximal and distal end, an inner elongated, flexible, member having a proximal end and a distal end, the inner member slidably disposed within the outer member. The system further comprises an electromagnet disposed on the distal end of one of the outer member and inner member, and a magnetically attractive element disposed on the distal end of another of the outer member and inner member. The magnetically attractive element is configured for magnetically interacting with the electromagnet to deflect the distal end of the inner member.

12 Claims, 6 Drawing Sheets

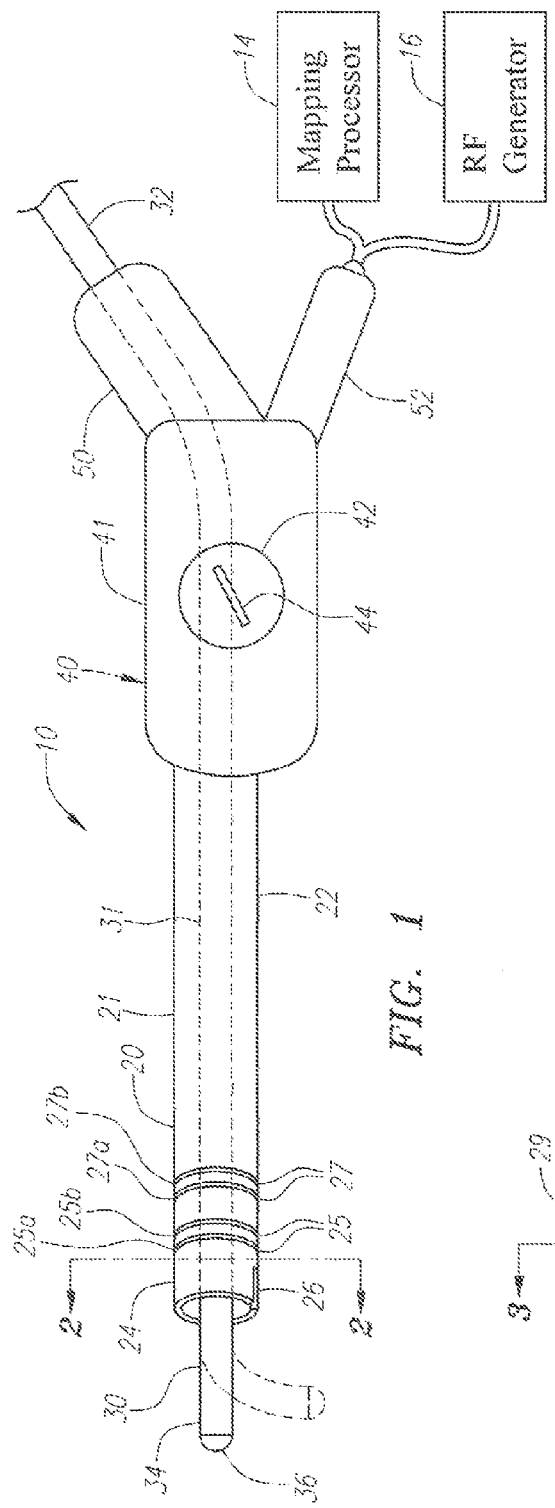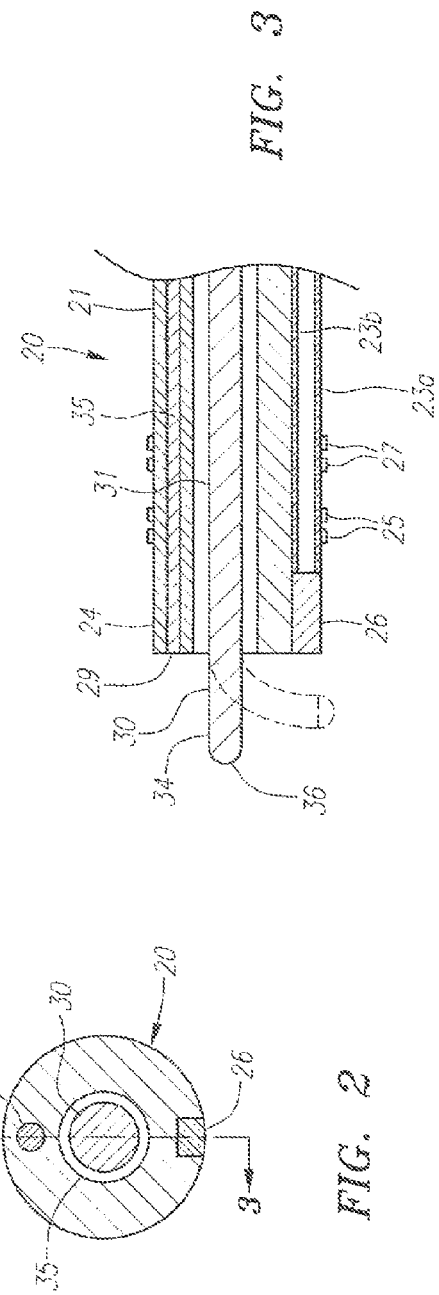
FIG. 1
FIG. 2
FIG. 3

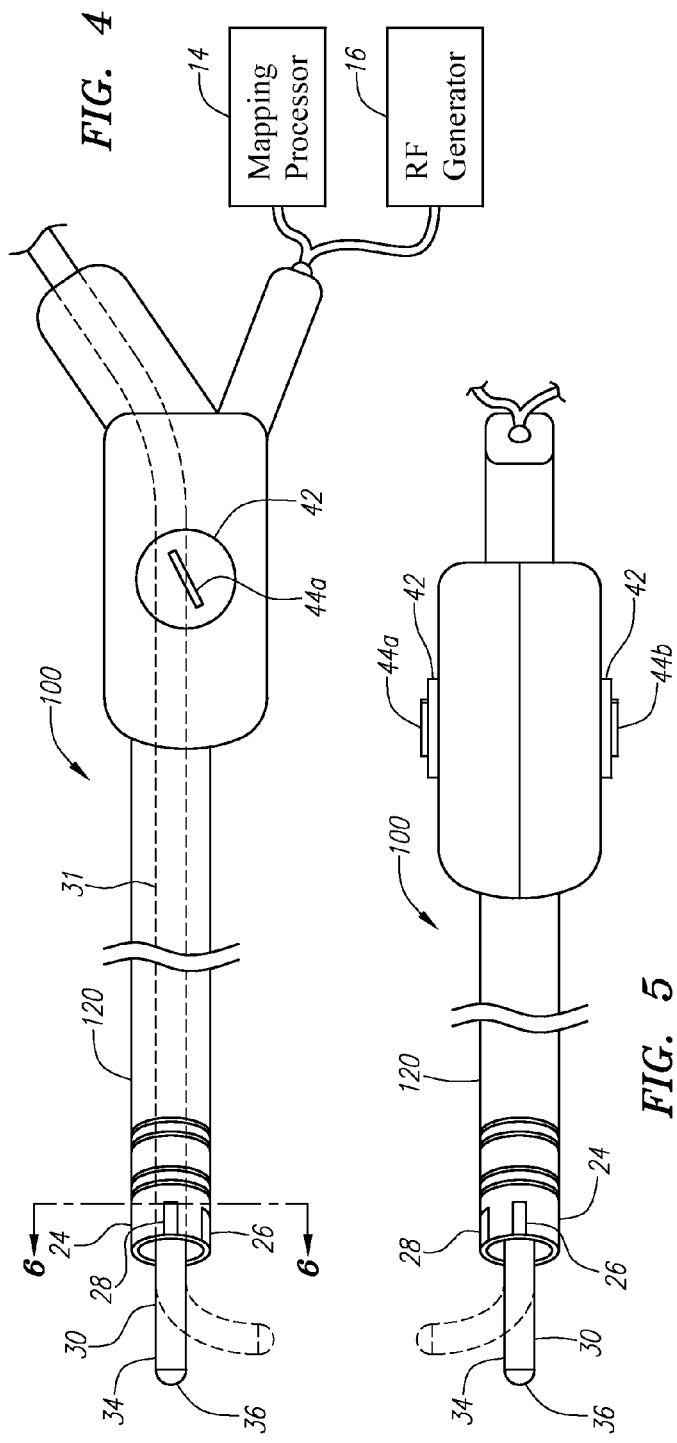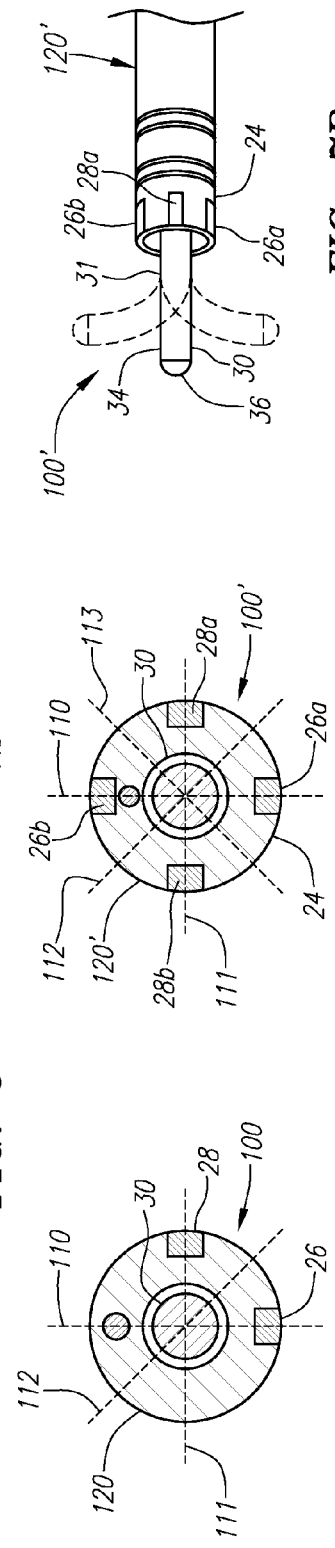

MAGNETICALLY STEERABLE CATHETER ASSEMBLY

RELATED APPLICATION DATA

The present application claims the benefit under 35 U.S.C. §119 to U.S. provisional patent application Ser. No. 60/957,999, filed Aug. 24, 2007. The foregoing application is hereby incorporated by reference into the present application in its entirety.

FIELD OF THE INVENTION

The present invention relates generally to apparatus and methods for introducing catheters within a patient, and more particularly, to apparatus and methods for steering catheters through the tortuous vasculature of the patient

BACKGROUND

Catheter/guidewire combinations are used in conventional methods to access internal anatomical structures via the vasculature of a patient. Many peripheral and cardiac procedures are routinely performed, including angiography, angioplasty, and stent placement. In many procedures the ability to properly access the target anatomical structure is hampered or even prevented by tortuous or tight vessels. In fact, tortuous anatomy presents the single greatest challenge to the skilled clinician. Difficult turns and angled vessels often make for difficult passage. Inability to access the correct location may ultimately result in treatment failure, increased patient risk, and/or increased time in performing the medical procedure.

A number of companies have developed, or are developing, systems designed to magnetically manipulate and steer catheters (and other medical devices) inside the human body. In particular, a strong magnetic field is applied to the distal end of a catheter, which carries one or more magnetic elements (either permanent or electromagnetic magnets, or magnetic material, such as ferrous material), so that the resulting magnetic force moves the distal end of the catheter. The magnitude and direction of the magnetic force is determined by several factors: (a) the strength of the magnetic field; (b) the orientation (direction and polarity) of the magnetic field; and (c) the characteristics of the magnetic element(s) in the catheter. By controlling the strength and orientation of the magnetic field (e.g., using gimbaled sets of electromagnets), the catheter can be steered within the body, and/or made to apply contact force to the tissue within the body. While magnetic navigation systems have been generally successful in steering catheters through the vasculature of a patient, they are costly, as well as large and cumbersome.

Accordingly, there remains a need to provide a steerable catheter capable of being more efficiently guided through the vasculature of a patient.

SUMMARY OF THE INVENTION

In accordance with a first aspect of the present inventions, a magnetically steerable catheter system comprises an outer elongated, flexible member (e.g., a catheter), an inner elongated, flexible, member (e.g., a guidewire) slidably disposed within the outer member, at least one electromagnet disposed on the distal end of one of the outer member and the inner member, and at least one magnetically attractive element (e.g., ferrous material) disposed on the distal end of another of the outer member and the inner member. The magnetically attractive element(s) is configured for magnetically interacting with the electromagnet(s) to deflect the distal end of the inner member. As examples, the distal end of the inner member may be preferentially deflected in only one plane or in at least two planes.

In one embodiment, the system further comprises an electrical connector and a magnetic steering mechanism mounted to the proximal end of the member on which the electromagnet(s) is disposed. The electrical connector may be electrically coupled to the electromagnet(s), and the magnetic steering mechanism may control the electrical energy delivered from the electrical connector to the electromagnet(s). For example, the magnetic steering mechanism may have a first position that prevents electrical energy from being delivered to the electromagnet(s), so that the distal end of the inner member is not deflected, and a second position that allows electrical energy to be delivered to the electromagnet(s), so that the distal end of the inner member is deflected. Or, the magnetic steering mechanism may have a first position that allows electrical energy to be delivered to the electromagnet(s) in a first polarity, so that the inner member is deflected in a first direction, and a second position that allows electrical energy to be delivered to the electromagnet(s) in a second polarity opposite to the first polarity, so that the inner member is deflected in a second direction opposite the first direction. The system may further comprise at least one medical operative element (e.g., one or both of a tissue ablative element and a tissue mapping element) disposed on the distal end of the outer member.

In accordance with a second aspect of the present inventions, a method of performing a medical procedure on a patient is provided. The method comprises introducing an outer elongated member within a vasculature of the patient, and introducing an inner elongated member within the vasculature. For example, the inner member may be initially introduced into the vasculature, and the outer member may be advanced over the inner member into the vasculature. The method further comprises moving the inner member within the outer member, and deflecting a distal end of the inner member within the vasculature by generating a magnetic field between the distal end of the inner member and a distal end of the outer member.

For example, the magnetic field may be generated by energizing an electromagnet disposed on the distal end of one of the outer member and inner member, and the magnetic field can attract or repel an element disposed on the distal end of another of the outer member and inner member. In one method, the distal end of the inner member is deflected within the vasculature along only one plane by generating the magnetic field in one direction. In another method, the distal end of the inner member is deflected within the vasculature along at least two planes by generating the magnetic field in at least two directions. In still another method, the distal end of the inner member is deflected within the vasculature in a first direction by generating the magnetic field with a first polarity, and deflected within the vasculature in a second direction opposite to the first direction by generating the magnetic field with a second polarity opposite the first polarity.

The method may comprise rotating the inner member while the distal end of the inner member is deflected. In an optional method, the inner member is deflected within the vasculature to steer the inner member within the vasculature. The method may further comprise placing the distal end of the outer member adjacent a target site, and performing at least one medical function (e.g., one or both of a tissue ablation function and a tissue mapping function) at the target tissue site.

Other features of the present invention will become apparent from consideration of the following description taken in conjunction with the accompanying drawings.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIG. 1 is a perspective view of a first preferred embodiment of a magnetically assisted steering catheter system, in accordance with the present invention;

FIG. 2 is a cross-sectional detail of a distal end of the system of FIG. 1, showing a guidewire inserted through the system;

FIG. 3 is a cross-section of the system of FIG. 2, taken along line 3-3;

FIG. 4 is a perspective view of an alternative embodiment of the apparatus of FIG. 1, having four degrees of steering;

FIG. 5 is a bottom view of the system of FIG. 4;

FIG. 6 is a cross-section view of the system of FIG. 4, taken along line 6-6;

FIG. 7A is a cross-section view of another alternative embodiment of a magnetically assisted steering catheter/guidewire apparatus, in accordance with the present invention;

FIG. 7B is a side view of another alternative embodiment of a magnetically assisted steering catheter/guidewire apparatus, in accordance with the present invention.

DETAILED DESCRIPTION OF THE ILLUSTRATED EMBODIMENTS

Figure 8A:
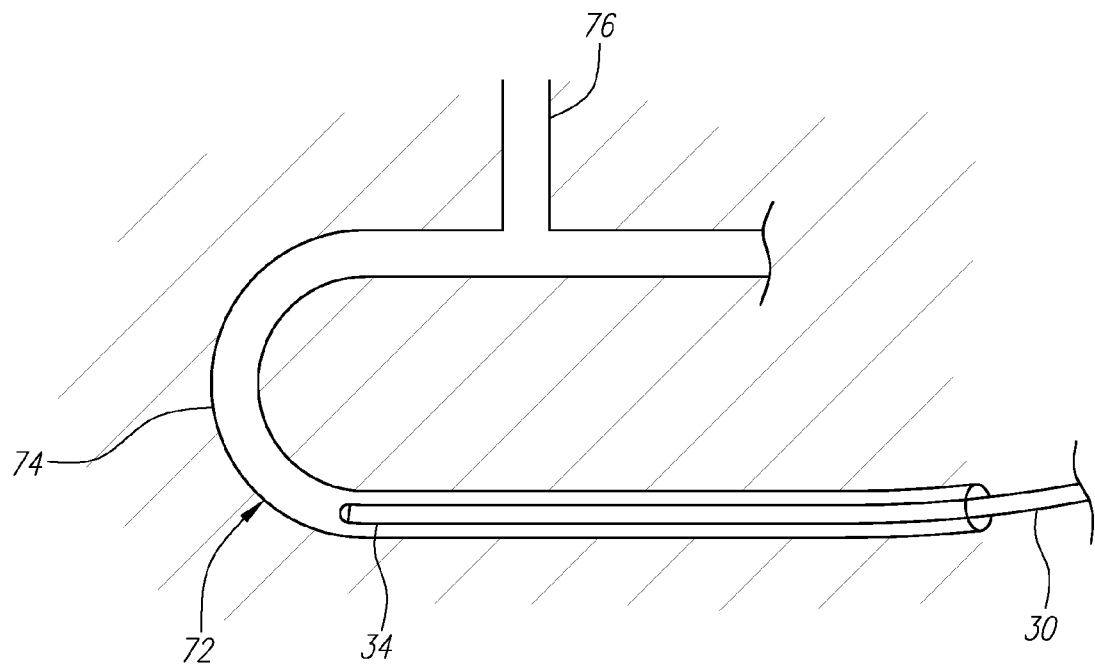
FIGS. 8A-8H are plan views of a method of using the magnetically assisted steering catheter system of FIG. 1 to maneuver through a tortuous vein into a heart.

Referring to FIG. 1, a magnetically assisted steering catheter system 10 constructed in accordance with the present invention is shown. The system 10 generally comprises (a) an ablation/mapping catheter 20 configured to be introduced through the vasculature of the patient, and into a three-dimensional anatomical cavity, and in particular, a chamber of the heart, where it can be used to ablate and map heart tissue; (b) an electrophysiology mapping processor 14 used to electrophysiologically map heart tissue with the catheter 20 in order to identify arrhythmia causing substrates; (c) a source of ablation energy, and in particular, a radio frequency (RF) generator 16, for delivering ablation energy to the catheter 20 in order to ablate the identified substrates, and (d) a guidewire 30 for facilitating introduction of the catheter 20 through the tortuous vasculature of the patient.

The processor 14 is configured to detect, process, and record electrical signals within the heart. Based on these electrical signals, a physician can identify the specific target tissue sites within the heart to be ablated, and to ensure that the arrhythmia causing substrates within the heart have been destroyed by the ablative treatment. Such mapping techniques are well known in the art. The RF generator 16 is configured to deliver ablation energy to the catheter 20 in a controlled manner in order to ablate the target tissue sites identified by the mapping processor. Alternatively, other types of ablative sources besides the RF generator 16 can be used, e.g., a microwave generator, an ultrasound generator, a cryoablation generator, and a laser or other optical generator. Ablation of tissue within the heart is well known in the art, and thus for purposes of brevity, the RF generator 16 will not be described in further detail. Further details regarding generator are provided in U.S. Pat. No. 5,383,874, which is expressly incorporated herein by reference. Alternatively, the mapping processor 14 and the RF generator 16 can be incorporated into a single integrated device, instead of the discrete components shown in FIG. 1.

Referring further to FIGS. 2 and 3, the guidewire 30 is configured to be slidably disposed within the catheter 20, as will be described in further detail below. The guidewire 30 comprises an elongate flexible body 31 having a proximal end 32 and a distal end 34. The guidewire body 31 is composed of a flexible and resilient material, for example, a superelastic alloy such as Nitinol, or alternatively is composed of a material such as titanium, tantalum, or stainless steel. The outer diameter of the guidewire body 31 is approximately 0.020 inches (0.51 mm). The length of the guidewire body 31 is sufficient to pass through the entire length of the catheter 20. In an exemplary embodiment, the length of the guidewire body 31 is approximately 180 to 220 cm.

The guidewire 30 further comprises a magnetically attractive element 36 disposed on the distal end 34 of the guidewire 30. The magnetically attractive element 36 may be secured to the distal end 34 by welding, brazing, gluing, other suitable adhesive, and the like. The magnetically attractive element 36 can take the form of an element that moves in response to a magnetic field. For example, the magnetically attractive element 36 can comprise a permanent magnetic material, such as neodymium-iron-boron, or can comprise a ferrous material, such as cold rolled steel or iron-cobalt alloy. The magnetically attractive element 36 can also take the form of an electromagnet connected to wires (not shown) that are passed in conventional fashion through a lumen (not shown) extending through the guidewire 30.

The catheter 20 generally comprises an elongate flexible catheter body 21 having a proximal end 22 and a distal end 24, and a guidewire lumen 35 extending through the length of the catheter body 21. The guidewire lumen 35 is sized to receive the guidewire 30. In the illustrated embodiment, the catheter body 21 comprises a unibody design; that is, it is formed from a single extrusion in accordance with methods used by a person of ordinary skill in the art. Alternatively, a two piece catheter body (not shown), such as a proximate member (not shown) and a distal member (not shown) may be bonded together at an interface (not shown) with an overlapping thermal bond or adhesively bonded together end to end over a sleeve in what is referred to as a "butt bond."

In the illustrated embodiment, the catheter body 21 is about 5 to 9 French in diameter with a length about 80 cm to 115 cm. The catheter body 21 is composed of a biocompatible thermoplastic material, such as Pebax® material (polyether block amide) and stainless steel braid composite, which has good torque transmission properties. In some implementations, an elongate guide coil (not shown) may also be provided within the catheter body 21. The distal end 24 of the catheter body 21 preferably includes a radiopaque compound, such as barium, so that the catheter 20 can be observed using fluoroscopic or ultrasound imaging, or the like. Alternatively, radio-opaque markers (not shown) can be place along the distal end 24 of the catheter body 21.

The catheter body 21 has a resilient structure that facilitates the functionality of the magnetically assisted steering catheter system 10. To this end, the catheter 20 includes a spring member 29 positioned inside of and passing through the length of the catheter body 21. The shape of the catheter body 21 is achieved through the use of the spring member 29. To improve the torqueability of the catheter body 21, which is important to the predictable and controlled movement of the distal end 24, the spring member 29 in the illustrated embodiment is formed of a unibody structure, and affixed so that a torsional force applied to the proximal end 22 is transmitted to the distal end 24 of the catheter body 21 without significant loss.

The catheter 20 further comprises an electromagnet 26 carried by the distal end 24 of the catheter body 21, one or more operative elements, and in particular, a tissue ablative element 25 and a mapping element 27 carried by the distal end 24 of the catheter body 21, and a handle assembly 40 mounted to the proximal end 22 of the catheter body 21.

The electromagnet 26 may take the form of a coiled solenoid or an induction electromagnet secured to the distal end 24 using suitable means, such as by welding, brazing, gluing, other suitable adhesive, and the like, depending on the materials from which the electromagnet 26 and the catheter body 21 are made. The catheter 20 further comprises two leads 23a, 23b extending through the catheter body 21 from the electromagnet 26 towards the proximal end 22 of the catheter body 21 for coupling to a source of electrical energy, which may be incorporated into the RF generator 16 or a separate unit (not shown).

Electrical current is supplied to the electromagnet 26 via lead wire 23a and returned by return wire 23b to induce a first magnetic field. Polarity through the electromagnet 26 is reversed to induce a second magnetic field in an opposite direction from the first magnetic field. The electromagnet 26 is configured for generating a sufficient magnetic field to deflect (shown in phantom in FIGS. 1-3) or otherwise manipulate the magnetically attractive element and/or tip 36 on the distal end 34 of the guidewire 30. The electromagnet 26 may be configured to generate higher magnetic fields for heavier guidewires, and/or guidewires that have distal ends 34 further away from the electromagnet 26.

The strength of the magnetic field generated by the electromagnet 26 depends upon a number of factors, such as the geometry of the electromagnet 26, the material from which the electromagnet 26 is made, and/or the amount of power supplied to the electromagnet 26. In the illustrated embodiment, the power delivered to the electromagnet 26 is fixed at a set level when activated to deliver sufficient power to deflect (shown in phantom in FIGS. 1-3) the guidewire tip 36 within a prescribed distance from the electromagnet 26. Alternatively, the power delivered to the electromagnet 26 may be adjustable. In this case, during use, the power is incrementally increased until a desired magnetic field intensity is achieved, and therefore sufficient to deflect the guidewire tip 36 an incremental distance from the electromagnet 26.

In another embodiment, the electromagnet 26 may include a plurality of portions with each portion electrically isolated from the other portion(s). Each of the portions can be electrically connected to the source of energy (not shown), and may be individually or collectively activated to generate a magnetic field. If a weak magnetic field is desired, then only one of the portions is activated. If a relatively stronger magnetic field is desired, then one or more additional portions are activated. Further details on one embodiment of the electromagnet 26 are disclosed in U.S. Pat. No. 6,961,620, which is expressly incorporated herein by reference.

In alternative embodiments, the distal end 24 of the catheter body 21 can carry the magnetically attractive element 36 instead of the electromagnet 26, and the distal end 34 of the guidewire body 31 can carry the electromagnet 26 instead of the magnetically attractive element 36.

In the illustrated embodiment, the tissue ablative element 25 takes the form of a linear electrode assembly that includes ring electrodes 25a, 25b mounted on the distal end 24. Notably, the split nature of the ablative element 25 provides selective monopolar and bipolar functionality to the catheter 20. That is, one or both of the ring electrodes 25a, 25b can be configured as one pole of a monopolar arrangement, so that ablation energy emitted by one or both of the electrodes 25a, 25b is returned through an indifferent patch electrode (not shown) externally attached to the skin of the patient; or the ring electrodes 25a, 25b can be configured as two poles of a bipolar arrangement, in which energy emitted by one of the ring electrodes 25a, 25b is returned to the other electrode. In addition to serving as a selective unipolar/bipolar means of ablation, alternatively the ring electrodes 25a, 25b may also serve as a closely spaced high resolution pair of mapping electrodes. The combined length of the ablation electrodes 25a, 25b is preferably about 6 mm to about 10 mm in length. In one embodiment, each ablation electrode 25a, 25b is about 4 mm in length with 0.5 mm to 3.0 mm spacing, which will result in the creation of continuous lesion patterns in tissue when coagulation energy is applied simultaneously to the electrodes 25a, 25b.

In the illustrated embodiment, the ablation electrodes 25a, 25b comprise solid rings of conductive material, like platinum, or can comprise a conductive material, like platinum-iridium or gold, coated upon the device using conventional coating techniques or an ion beam assisted deposition (IBAD) process. For better adherence, an undercoating of nickel or titanium can be applied. Any combination of the electrodes can also be in the form of helical ribbons or formed with a conductive ink compound that is pad printed onto a nonconductive tubular body. A preferred conductive ink compound is a silver-based flexible adhesive conductive ink (polyurethane binder), however other metal-based adhesive conductive inks such as platinum-based, gold-based, copper-base, etc., is also contemplated. Such inks are more flexible than epoxy-based inks.

The ablation electrodes 25a, 25b may alternatively comprise a porous material coating, which transmits coagulation energy through an electrified ionic medium. For example, as disclosed in U.S. Pat. No. 5,991,650, ablation electrodes may be coated with regenerated cellulose, hydrogel or plastic having electrically conductive components. With respect to regenerated cellulose, the coating acts as a mechanical barrier between the surgical device components, such as electrodes, preventing ingress of blood cells, infectious agents, such as viruses and bacteria, and large biological molecules such as proteins, while providing electrical contact to the human body. The regenerated cellulose coating also acts as a biocompatible barrier between the device components and the human body, whereby the components can now be made from materials that are somewhat toxic (such as silver or copper).

The ablation electrodes 25a, 25b are electrically coupled to individual wires (not shown) disposed within the catheter 20 where the wires (not shown) are electrically coupled either directly to a connector (not shown) that is received in a port on the handle assembly 40 or indirectly to the connector via a PC board (not shown) in the handle assembly 40. The connector (not shown) plugs into the RF generator 16 (shown in FIG. 1). Although ablation electrodes 25a, 25b have been described as the operative elements that create the lesion, other operative elements, such as elements for chemical ablation, laser arrays, ultrasonic transducers, microwave electrodes, and ohmically heated hot wires, and such devices may be substituted for the electrodes 25a, 25b.

The catheter 20 may optionally comprise temperature sensors (not shown), such as thermocouples or thermistors, which may be located on, under, abutting the longitudinal end edges of, or in between, the electrodes 25a, 25b. In some embodiments, a reference thermocouple (not shown) is also provided. For temperature control purposes, signals from the temperature control sensors can be transmitted to the RF generator 16 by way of wires (not shown) that are also connected to the aforementioned PC board in the handle assembly 40. Suitable temperature sensors and controllers, which control power to electrodes based on a sensed temperature, are disclosed in U.S. Pat. Nos. 5,456,682, 5,582,609 and 5,755,715.

In the illustrated embodiment, the mapping element 27 takes the form of a pair of ring electrodes 27a, 27b that are mounted on the distal end 24 of the catheter body 21 proximal to the ablative element 25. Optionally, additional pairs of ring electrodes can be located along the distal end 24 of the catheter body 21. The mapping electrodes 27a, 27b comprise a solid, electrically conducting material, like platinum or gold, attached about the catheter body 21. Alternatively, the mapping electrodes 27a, 27b can be formed by coating the exterior surface of the catheter body 21 with an electrically conducting material, like platinum or gold. The coating can be applied using sputtering, ion beam deposition, or equivalent techniques. The mapping electrodes 27a, 27b can have suitable lengths, such as between 0.5 and 5.0 mm. In use, the mapping electrodes 27a, 27b sense electrical events in myocardial tissue for the creation of electrograms, and are electrically coupled to the mapping processor 14 (shown in FIG. 1). A signal wire (not shown) is electrically coupled to each mapping electrode 27a, 27b, and the wires (not shown) extend through the catheter body 21 into an external multiple pin connector (not shown) located on the handle assembly 40, which electrically couples the mapping electrodes 27a, 27b to the mapping processor 14.

The handle assembly 40 comprises a handle 41, a steering mechanism 42, an electrical connector 52, and a guidewire port 50 associated with the handle 41. The handle 41 is preferably composed of a durable and rigid material, such as medical grade plastic, and is ergonomically molded to allow a physician to more easily manipulate the catheter 20. The steering mechanism 42 includes a steering switch 44 configured to be actuated from a first position (off), which prevents electrical energy from the energy source from energizing the electromagnet, to a second position (on), which allows electrical energy from the energy source (not shown) to energize the electromagnet 26. As a result, the energized electromagnet 26 pulls the magnetically attractive element 36, thereby deflecting the distal end 34 of the guidewire body 31 from a straight geometry to form a simple curve (i.e., a curve that lies in a single plane) (shown in phantom in FIGS. 1-3). The steering switch 44 is configured to be actuated back to the off position to allow the resiliency of the guidewire body 31 to flex itself back into a straight geometry.

Although the steering mechanism 42 has been described as unilaterally bending the proximal end 34 of the guidewire body 31 into the curved geometry, the steering mechanism 42 could be modified to bilaterally bend the distal end 34 of the guidewire 30 into two opposite curved geometries along a single plane, e.g. by actuating the steering switch 44 to a third position, that energizes the electromagnet 26 with a reverse polarity. As a result, the energized electromagnet 26 may push the magnetically attractive element 36, thereby deflecting the distal end 34 of the guidewire body 31 opposite the aforementioned simple curve. In this case, the off position may be between the two on positions, such that the switch 44 must pass through the off position when changing the polarity of the electromagnet 26.

In the illustrated embodiment, the guidewire port 50 may comprise a luer lock connector (not shown) through which the guidewire 30 is introduced. Optionally, the guidewire port 50 may have numerous uses in addition to facilitating introduction of the guidewire 30. For example, the guidewire port 50 can provide access for the introduction of other flexible elongate tools or apparatus during a surgical procedure, and can provide a connection to a source of fluid such as saline or contrast (not shown). The conduit 52 facilitates electrical connectivity of the operative elements of the catheter 20 with the processor 14, the RF generator 16 and the source of energy (not shown) by providing a path for conductors or wires (not shown). The wires (not shown) may couple to the aforementioned connector (not shown) or the PC board (not shown).

Referring to FIG. 4-6, another embodiment of a magnetically assisted steering catheter system 100 constructed in accordance with the present invention is shown. The system 100 is similar to the previously described system 10 in that it comprises a catheter 120, a guidewire 30, a mapping processor 14, and a radio frequency (RF) generator 16. The guidewire 30, the mapping processor 14, and the radio frequency (RF) generator 16 are constructed in a similar manner as the previously described guidewire 30, mapping processor 14, and RF generator 16, and thus, for purpose of brevity, the details of their construction are not repeated herein. The catheter 120 differs from the previously described catheter 20 in that it comprises two electromagnets 26, 28 instead of the single electromagnet 26, and a dual-steering mechanism 42.

The electromagnets 26, 28 are provided on a distal end 24 of the catheter 120, and may be a coiled solenoid or an induction electromagnet. Further, as best seen in FIG. 6, the electromagnets 26, 28 are disposed on the distal end 24, such that they are circumferentially offset 90 degrees from each other.

The dual steering mechanism 42 comprises a pair of steering switches 44a, 44b. The steering switch 44a is actuated from a first position (off), which prevents electrical energy from the energy source (not shown) from energizing the electromagnet 26, to a second position (on), which allows electrical energy from the energy source to energize the electromagnet 26. Likewise, steering switch 44b is actuated from a first position (off), which prevents electrical energy from the energy source (not shown) from energizing the electromagnet 28, to a second position (on), which allows electrical energy from the energy source to energize the electromagnet 28. The energized electromagnet 26 pulls a magnetically attractive element 36 deflecting a distal end 34 of a guidewire body 31 from a straight geometry to form a first simple curve (shown in phantom in FIG. 4), and the energized electromagnet 28 pulls the magnetically attractive element 36 deflecting the distal end 34 of the guidewire body 31 from a straight geometry to form a second simple curve, which is 90 degrees offset from the first simple curve (shown in phantom in FIG. 5). The steering switches 44a, 44b are actuated back to the initial position to allow the resiliency of the guidewire body 31 to flex itself back into a straight geometry. The steering switches 44a, 44b can be actuated separately, or alternatively, the steering switches 44a, 44b can be actuated simultaneously.

Actuated separately, the steering switches 44a, 44b facilitate deflecting the distal end 34 of the guidewire body 31, in a plurality of planes 110, 111 respectively associated with the electromagnets 26, 28, as shown in FIG. 6. In the illustrated embodiment, the planes 110, 111 are offset 90 degrees from each other such that the distal end 34 of the guidewire body 31 can be preferentially deflected in a single direction along the plane 110, and a single direction along the plane 111; that is, in two directions offset from each other by 90 degrees. Actuated simultaneously, the switches 44a, 44b facilitate deflecting the distal end 34 of the guidewire body 31, from a combined magnetic force, pulling the magnetically attractive element 36 in a plane 112 angled between the electromagnets 26, 28; that is equal-distant between the planes 110, 111, such that the distal end 34 of the guidewire body 31 can be preferentially deflected in a single direction along the plane 112.

The dual steering mechanism 42 is described as unilaterally bending the proximal end 34 of the guidewire body 31 towards electromagnets 26, 28. However, the dual steering mechanism 42 could be modified to bilaterally bend the distal end 34 of the guidewire body 31 into two opposite curved geometries, e.g. by actuating the steering switches 44a, 44b to a third position, that energizes the electromagnets 26, 28 with a reverse polarity. As a result, the energized electromagnets 26, 28 push the magnetically attractive element 36, thereby deflecting the distal end 34 of the guidewire body 31 opposite the aforementioned simple curves. In this case, the off position may be between the two on positions, such that the switches 44a, 44b must pass through the off position when changing the polarity of the electromagnets 26, 28. Thus, when the steering switches 44a, 44b are actuated separately with two polarities, the distal end 34 of the guidewire body 31 can be preferentially deflected in two opposite directions along the plane 110, and two opposite directions along the plane 111; that is, in four directions offset from each other by 90 degrees. When the steering switches 44a, 44b are actuated simultaneously with two polarities, the distal end 34 of the guidewire body 31 can be preferentially deflected in two opposite directions along the plane 112; that is, in two directions offset from each other by 180 degrees. It can be appreciated that when the switches 44a, 44b are both separately and simultaneously actuated, the distal end 34 of the guidewire body 31 can be preferentially deflected in six directions.

Referring to FIGS. 7A and 7B, an alternative embodiment of a catheter 120' will now be described. The catheter 120' differs from the previously described catheter 120 in that it comprises four electromagnets 26a, 26b, 28a, 28b instead of the two electromagnets 26, 28. The electromagnets 26a, 26b, 28a, 28b are constructed in a similar manner as the previously described electromagnet 26. In the illustrated embodiment, the electromagnets 26a, 26b, 28a, 28b are disposed on the distal end 24, such that they are circumferentially offset 90 degrees from each other. The catheter 120' also differs from the previously described dual steering mechanism 42 in that each steering switch 44a, 44b may be modified to control two of the electromagnets.

For example, the steering switch 44a may be actuated from a first position (off), which prevents electrical energy from the energy source (not shown) from energizing the electromagnet 26a, to a second position (on), which allows electrical energy from the energy source to energize the electromagnet 26a. The energized electromagnet 26a pulls a magnetically attractive element 36 deflecting a distal end 34 of a guidewire body 31 from a straight geometry to form a first simple curve (shown in phantom in FIG. 7B). In contrast, the steering switch 44a is actuated from the first position (off), which prevents electrical energy from the energy source (not shown) from energizing the electromagnet 26a, to a third position (on), which allows electrical energy from the energy source to energize the electromagnet 26b. The energized electromagnet 26b pulls the magnetically attractive element 36 deflecting the distal end 34 of a guidewire body 31 from a straight geometry to form a second simple curve (shown in phantom in FIG. 7B) opposite the first simple curve.

The steering switch 44b may be actuated from a first position (off), which prevents electrical energy from the energy source (not shown) from energizing the electromagnet 28a, to a second position (on), which allows electrical energy from the energy source to energize the electromagnet 28a. The energized electromagnet 28a pulls a magnetically attractive element 36 deflecting a distal end 34 of the guidewire body 31 from a straight geometry to form a third simple curve (not shown). In contrast, the steering switch 44b is actuated from the first position (off), which prevents electrical energy from the energy source (not shown) from energizing the electromagnet 28a, to a third position (on), which allows electrical energy from the energy source to energize the electromagnet 28b. The energized electromagnet 28b pulls the magnetically attractive element 36 deflecting the distal end 34 of a guidewire body 31 from a straight geometry to form a forth simple curve (not shown) opposite the third simple curve.

The steering switches 44a, 44b are actuated back to the first position to allow the resiliency of the guidewire body 31 to flex itself back into a straight geometry. The first position may be between the two on positions, such that the switch 44a must pass through the off position when changing between electromagnets 26a, 26b. Likewise, the switch 44b must pass through the off position when changing between electromagnets 28a, 28b.

The steering switches 44a, 44b can be actuated separately, or alternatively, the steering switches 44a, 44b can be actuated simultaneously. Actuated separately, the steering switches 44a, 44b facilitate deflecting the distal end 34 of the guidewire body 31, in a plurality of planes 110, 111 (FIG. 7A), where the plane 110 is associated with each of the electromagnets 26a, 26b, and the plane 111 is associated with each of the electromagnets 28a, 28b. In the illustrated embodiment, the planes 110, 111 are offset 90 degrees from each other, such that the distal end 34 of the guidewire body 31 can be preferentially deflected in two opposite directions along the plane 110, and two opposite directions along the plane 111; that is, in four directions offset from each other by 90 degrees. Actuated simultaneously, the switches 44a, 44b facilitate deflecting the distal end 34 of the guidewire body 31, from a combined magnetic force from one of electromagnets 26a, 26b with one of electromagnets 28a, 28b, pulling the magnetically attractive element 36 in a plurality of planes 112, 113 that is equal-distant between the planes 110, 111, such that the distal end 34 of the guidewire body 31 can be preferentially deflected in two opposite directions along the plane 112, and two opposite directions along the plane 113; that is, in four directions offset from each other by 90 degrees. It can be appreciated that when the switches 44a, 44b are both separately and simultaneously actuated, the distal end 34 of the guidewire body 31 can be preferentially deflected in eight directions offset from each other by 45 degrees.

Having described the structure of the magnetically assisted steering catheter system 10, its operation in identifying and destroying arrhythmia causing substrates within the right ventricle RV of a heart H, as well as steering through the tortuous vasculature of the patient will now be described with reference FIGS. 8A-8G. It should be noted that the views of interior regions of the body described herein are not intended to be anatomically accurate in every detail. The figures show anatomic details in diagrammatic form as necessary to show the features of the embodiment described herein.

First, the guidewire 30 is introduced into the tortuous vein 72 until the guidewire distal end 34 resides just short of a hairpin turn 74 (FIG. 8A). In the illustrated embodiment, the tortuous vein 72 may be the patient's inferior vena cava such as those located near the right ventricle of the patient's heart. The system 10 is not limited to use in veins of the heart, and may be used in accessing tortuous veins in other locations of the patient's anatomy.

Figure 8B:
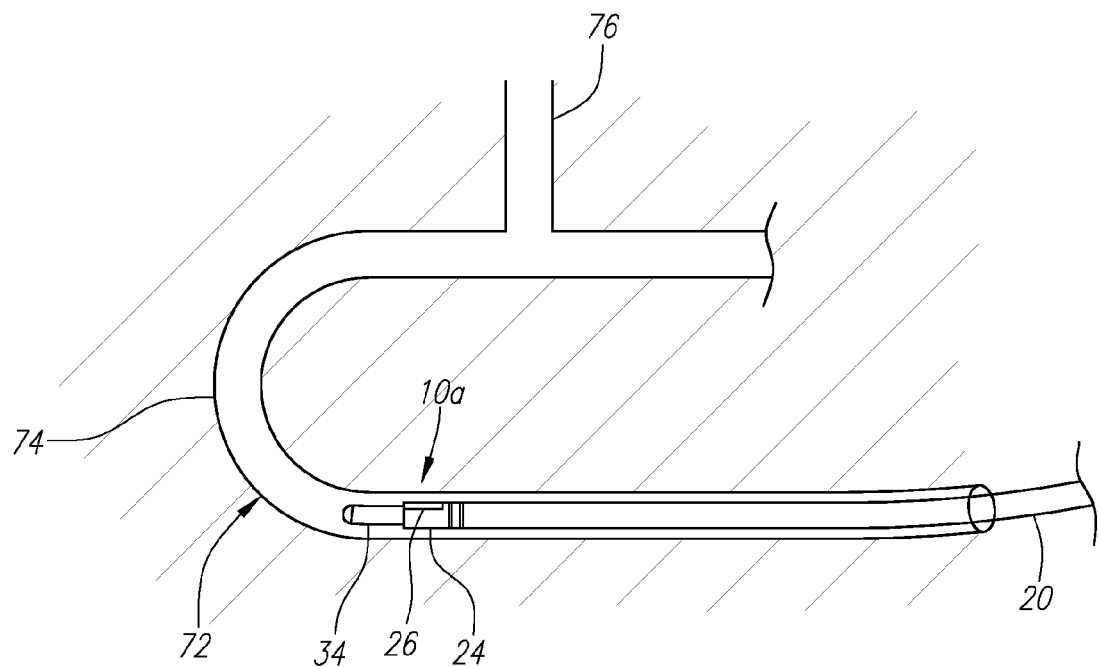
Figure 8C:
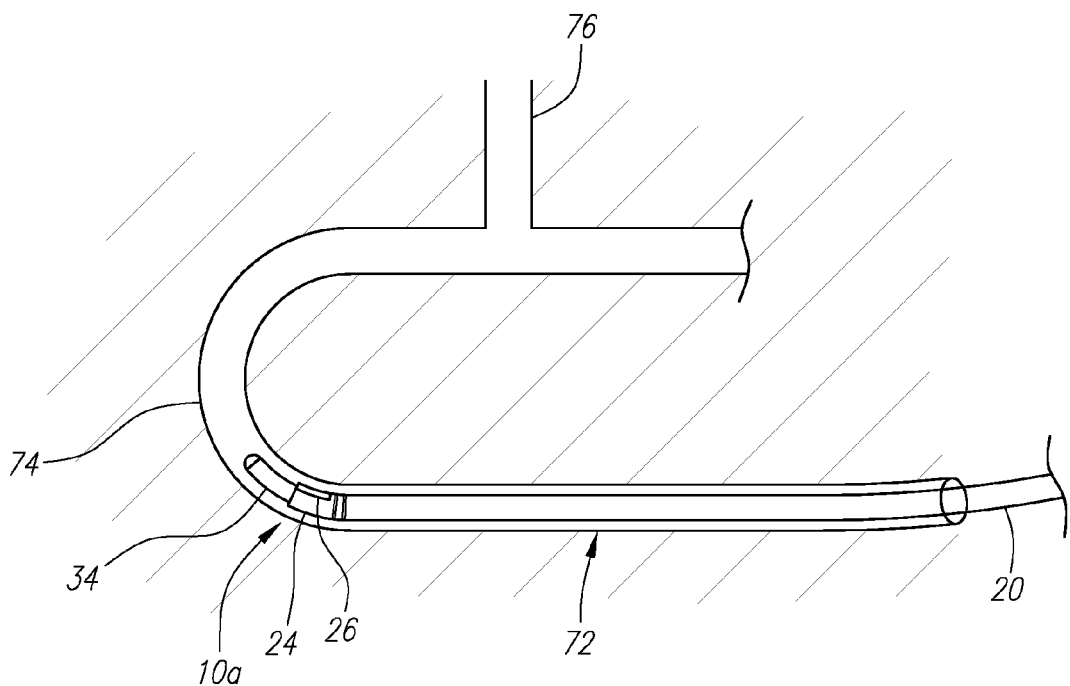

After the guidewire distal end 34 resides just short of a hairpin turn 74, the catheter 20 is then introduced over the guidewire 30 until the catheter distal end 24 also resides within the tortuous vein 72 just short of the hairpin turn 74, thereby forming a magnetically assisted steering catheter/guidewire combination 10a (FIG. 8B). Once the catheter/guidewire combination 10a is properly located within the tortuous vein 72, the steering mechanism 42 is operated to deflect the guidewire distal end 34 towards and into the hairpin turn 74 (FIG. 8C). If the steering mechanism 42 is only capable of unilateral deflection of the guidewire distal end 34, the catheter 20 is rotated around its axis somewhat, so that the guidewire distal end 34 deflects in the proper direction toward the hairpin turn 74. If the steering mechanism 42 is capable of multi-lateral deflection of the guidewire distal end 34, no such rotation is required. In any event, radiopaque markers (not shown) on the catheter distal end 24 are used to assist in properly positioning the electromagnet 26. Alternatively, other imaging technology known by those of ordinary skill in the art may be used.

Figure 8D:
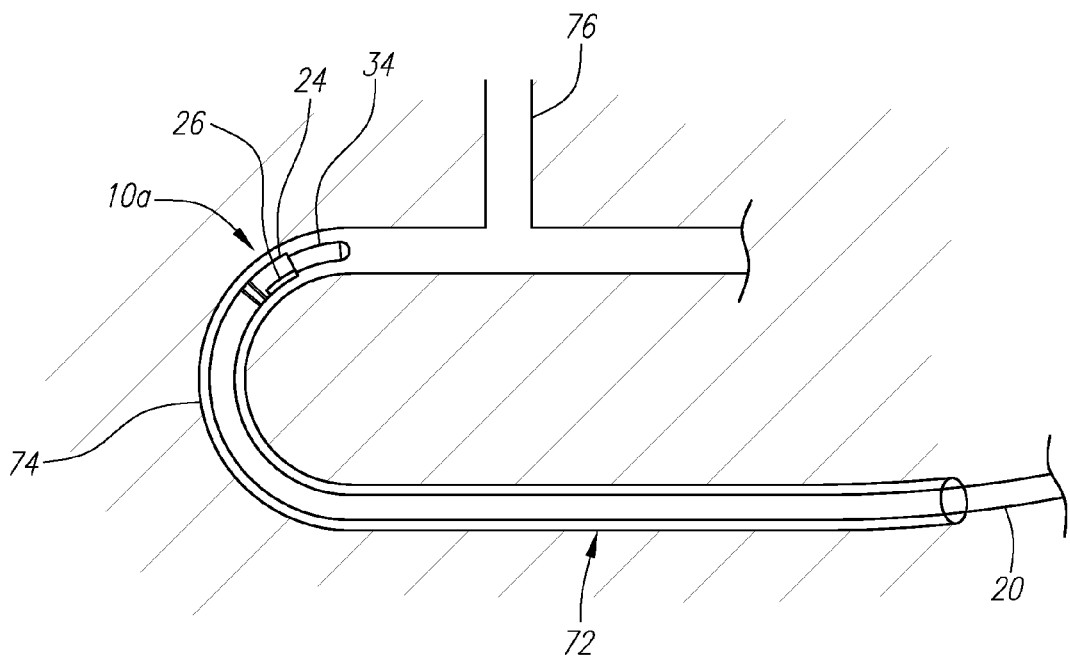

Once the guidewire distal end 34 is deflected towards and into the hairpin turn 74, the catheter/guidewire combination 10a is advanced so that the distal ends 24, 34 pass through the hairpin turn 74. The combination 10a is advanced through the hairpin turn 74 by maintaining the deflection of the distal end 34 into the hairpin turn 74, while the combination 10a is advanced further into the vein 72 (FIG. 8C). The steering mechanism 42 is operated to straighten the distal end 34 after the distal ends 24, 34 have passed through the hairpin turn 74 (FIG. 8D). The combination 10a is advanced and is positioned just short of the branch 76.

Figure 8E:
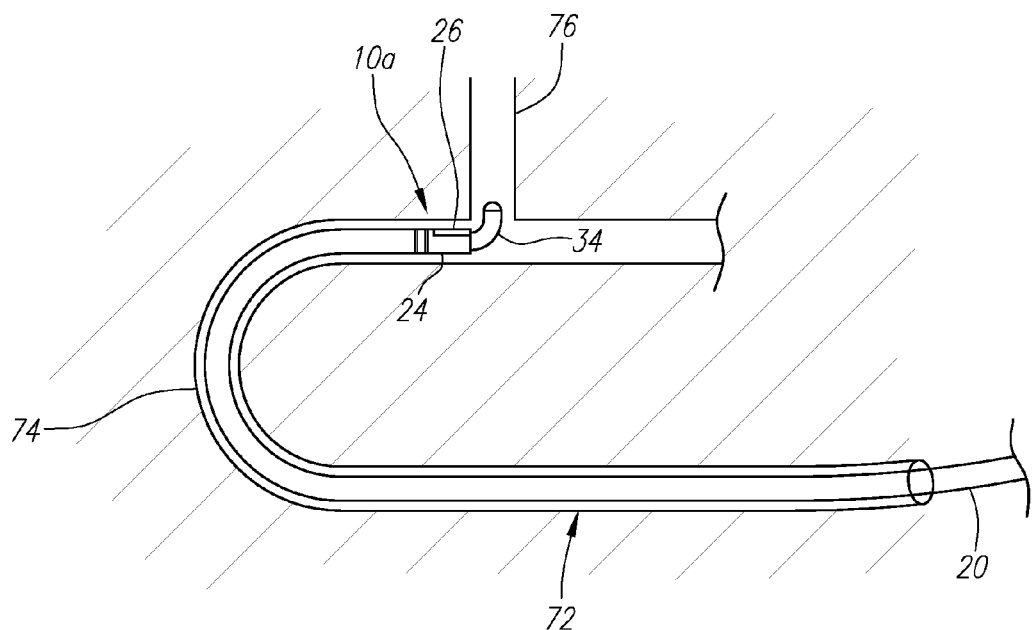
Figure 8F:
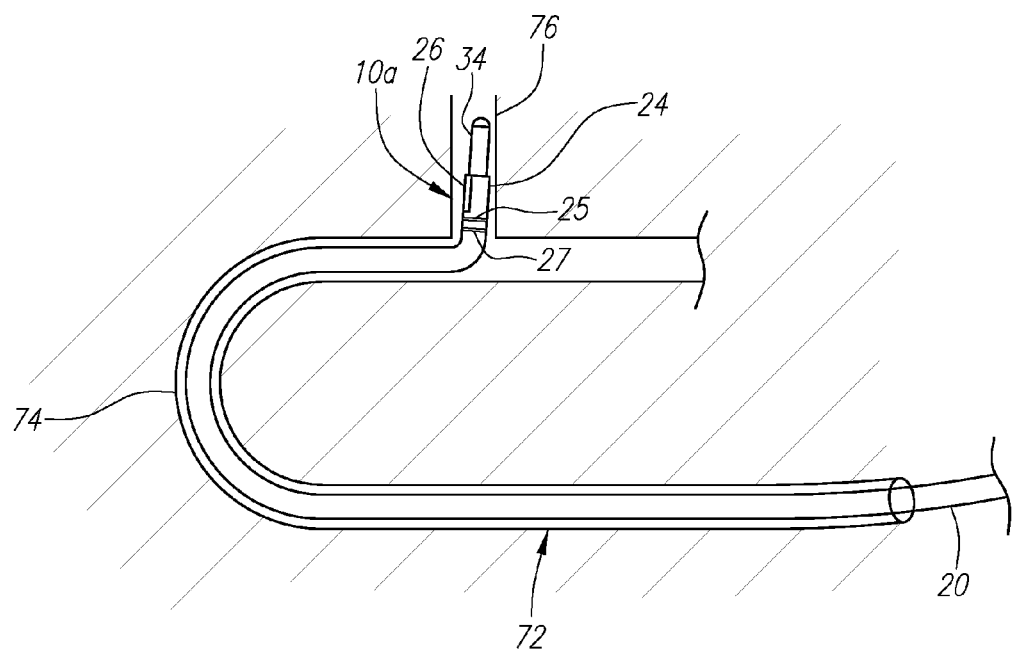

Once the distal ends 24, 34 of the combination 10a are properly placed just short of the branch 76, the steering mechanism 42 is operated in order to deflect the guidewire distal end 34 towards the branch 76 (FIG. 8E). If the steering mechanism 42 is only capable of unilateral deflection of the guidewire distal end 34, the catheter 20 is rotated around its axis somewhat, so that the guidewire distal end 34 deflects in the proper direction toward the branch 76. If the steering mechanism 42 is capable of multi-lateral deflection of the guidewire distal end 34, no such rotation is required. After the steering mechanism 42 is operated in order to deflect the guidewire distal end 34, the combination 10a is then advanced into the branch 76 so that the distal ends 24, 34 are positioned in the branch 76 (FIG. 8F).

Having traversed through the tortuous vein 72, the ablation/mapping catheter 20 may be positioned adjacent heart tissue suspected of containing arrhythmia causing substrates. The ablation/mapping catheter 20 may be used to reach heart tissue such as that in the left or right ventricle. The ablation/mapping catheter 20 can then be used to ablate and map the heart tissue.

Figure 8G:
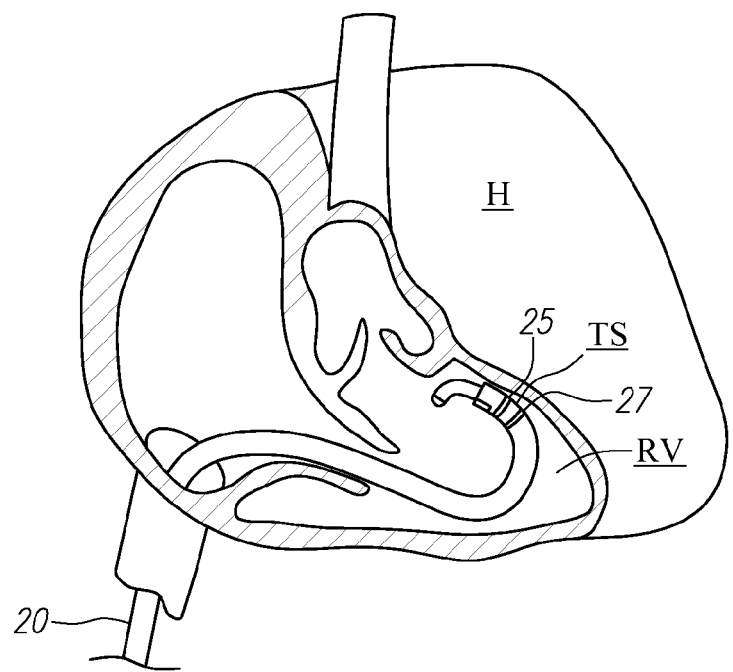
Figure 8H:
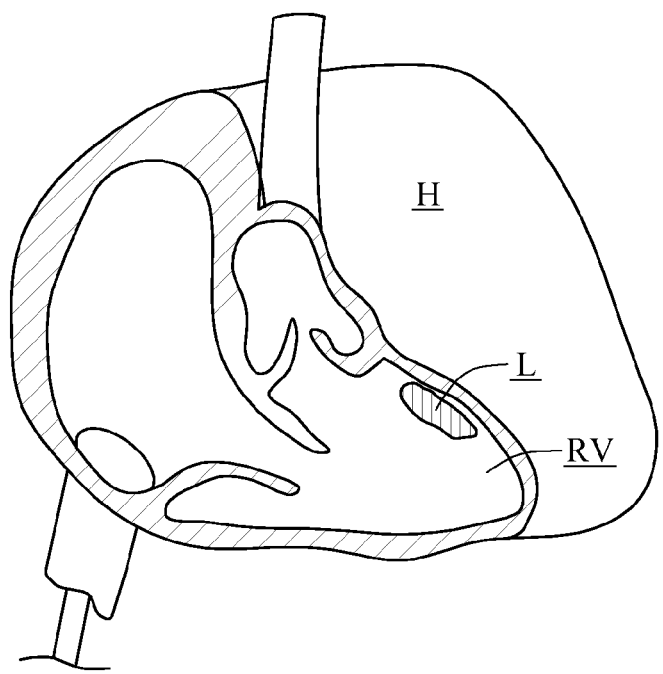

In particular, the ablation/mapping catheter 20 with the ablation/mapping elements 25, 27 of the ablation/mapping catheter 20 are firmly and stably placed in contact with a target tissue site TS in the right ventricle RV of the heart H (FIG. 8G). Then the mapping processor 14 (shown in FIG. 1) is operated in order to obtain and record ECG signals from the target tissue site TS, with the ablative element 25 serving as a mapping element to measure ECG signals in one region of the target tissue site TS, and the mapping element 27 serving to measure ECG signals in another region of the target tissue site TS. As described below, these ECG signals will be compared with the ECG signals obtained subsequent to an ablation procedure in order to determine if the resultant lesion has successfully destroyed the arrhythmia causing substrates in the right ventricle RV of the heart H Once the pre-ablation ECG signals have been obtained and recorded, the RF generator 16 (shown in FIG. 1) is operated in order to convey RF energy to the ablative element 25 (either in the monopolar or bipolar mode), thereby creating a linear lesion L (FIG. 8H). After the lesion has been created, the mapping processor 14 is again operated to obtain and record ECG signals form the target tissue site TS. These post-ablation ECG signals are compared to the pre-ablation ECG signals to determine whether an arrhythmia causing substrate at the target tissue site TS has been destroyed. Once proper ablation has been confirmed, additional tissue target sites can be mapped and ablated, e.g., by moving the ablation/mapping elements 25, 27 away from the original target tissue site and manipulating the catheter (e.g., by rotation) to place the ablation/mapping elements 25, 27 at another target tissue site. The steps illustrated in FIGS. 8G-8H can then be repeated.

Although particular embodiments of the present invention have been shown and described, it will be understood that it is not intended to limit the present invention to the preferred embodiments, and it will be obvious to those skilled in the art that various changes and modifications may be made without departing from the spirit and scope of the present invention. Thus, the present inventions are intended to cover alternatives, modifications, and equivalents, which may be included within the spirit and scope of the present invention as defined by the claims.

What is claimed is:

1. A magnetically steerable catheter system, comprising:
   an outer elongated, flexible member having a proximal and a distal end;
   an inner elongated, flexible, member having a proximal end and a distal end, the inner member slidably disposed within the outer member;
   at least one electromagnet disposed on the distal end of one of the outer member and the inner member; and
   at least one magnetically attractive element disposed on the distal end of another of the outer member and the inner member, the at least one magnetically attractive element configured for magnetically interacting with the at least one electromagnet to deflect the distal end of the inner member separately from the outer member.

2. The system of claim 1, wherein the outer member is a catheter.

3. The system of claim 2, wherein the inner member is a guidewire.

4. The system of claim 1, wherein the at least one magnetically attractive element comprises a ferrous material.

5. The system of claim 1, wherein the at least one magnetically attractive element is configured for magnetically interacting with the at least one electromagnet to preferentially deflect the distal end of the inner member along only one plane.

6. The system of claim 1, wherein the at least one magnetically attractive element is configured for magnetically interacting with the at least one electromagnet to preferentially deflect the distal end of the inner member along at least two planes.

7. The system of claim 1, further comprising an electrical connector mounted to the proximal end of the one of the outer member and inner member.

8. The system of claim 1, further comprising a magnetic steering mechanism disposed on the proximal end of at least one of the outer member and the inner member.

9. The system of claim 8, wherein the magnetic steering mechanism has a first position that prevents electrical energy from being delivered to the at least one electromagnet, such that the distal end of the inner member is not deflected, and a second position that allows electrical energy to be delivered to the at least one electromagnet, such that the distal end of the inner member is deflected.

10. The system of claim 8, wherein the magnetic steering mechanism has a first position that allows electrical energy to be delivered to the at least one electromagnet in a first polarity, such that the distal end of the inner member is deflected in a first direction, and a second position that allows electrical energy to be delivered to the at least one electromagnet in a second polarity opposite to the first polarity, such that the distal end of the inner member is deflected in a second direction opposite the first direction.

11. The system of claim 1, further comprising at least one medical operative element disposed on the distal end of the outer member.

12. The system of claim 11, wherein the at least one medical operative element comprises one or both of a tissue ablation element and a tissue mapping element.

* * * * *